United States Patent [19]

Ericsson et al.

[11] Patent Number: 4,778,758

[45] Date of Patent: Oct. 18, 1988

[54] DEVICE FOR SUSCEPTIBILITY TESTING OF MICROORGANISMS

[75] Inventors: Magnus Ericsson, Stockholm; Anne Bolmström, Åkersberga, both of Sweden

[73] Assignee: AB Biodisk, Solna, Sweden

[21] Appl. No.: 46,039

[22] PCT Filed: Jul. 28, 1986

[86] PCT No.: PCT/SE86/00344

§ 371 Date: Mar. 30, 1987

§ 102(e) Date: Mar. 30, 1987

[87] PCT Pub. No.: WO87/00858

PCT Pub. Date: Feb. 12, 1987

[30] Foreign Application Priority Data

Aug. 1, 1985 [SE] Sweden .............................. 8503676

[51] Int. Cl.[4] .............................................. C12Q 1/18
[52] U.S. Cl. ...................................... 435/32; 435/299; 435/810
[58] Field of Search ................... 435/30, 32, 292, 293, 435/294, 299, 805, 810, 300

[56] References Cited

U.S. PATENT DOCUMENTS

| | | | |
|---|---|---|---|
| 2,904,474 | 9/1959 | Förg | 435/30 X |
| 3,149,054 | 9/1964 | Ryan | 435/30 |
| 3,245,882 | 4/1966 | Guthrie | 435/29 |
| 3,509,026 | 4/1970 | Sanders | 435/33 |
| 3,510,263 | 5/1970 | Hach | 436/163 |
| 3,791,930 | 2/1974 | Saxholm | 435/33 |
| 3,843,452 | 10/1974 | Freake et al. | 435/294 |
| 3,932,223 | 1/1976 | Bucalo | 435/294 |
| 4,054,490 | 10/1977 | Vesterberg | 435/32 |
| 4,250,256 | 2/1981 | Wielinger et al. | 435/32 |
| 4,353,988 | 10/1982 | Couse et al. | 435/287 |

FOREIGN PATENT DOCUMENTS

| | | | |
|---|---|---|---|
| 2264089 | 10/1975 | France . | |
| 2331992 | 6/1977 | France | 435/294 |
| WO82/02251 | 7/1982 | PCT Int'l Appl. . | |

Primary Examiner—Samuel Scott
Assistant Examiner—Allen J. Flanigan
Attorney, Agent, or Firm—Cushman, Darby & Cushman

[57] ABSTRACT

A device for susceptibility testing of microorganisms comprising a transparent, sealable container (1), a rectangular carrier (3) coated with a growth medium, a sealing arrangment (2) for sealing the container (1), and a rectangular, transparent, non-porous, inert test strip (4) optionally provided with a grip. Two antimicrobial substances separated by a substance-free zone are applied on one side of the strip in concentration gradients exhibiting maxima and minima. On the other side of the test strip is a scale for direct reading of the susceptibility the above-mentioned concentration gradient(s) being pre-defined and adapted to the reading scale.

13 Claims, 1 Drawing Sheet

DEVICE FOR SUSCEPTIBILITY TESTING OF MICROORGANISMS

BACKGROUND OF THE INVENTION

The present invention is concerned with a device for susceptibility testing of microorganisms comprising a sealable container, a square carrier coated with a growth medium for microorganisms and a rectangular, transparent, non-porous, inert test strip, on one side of which is applied two antimicrobial substances separated by a zone free of substance, and on the other side of which is a scale for direct reading of the susceptibility.

Susceptibility testing of microorganisms is carried out by exposing the antibiotic(s) and/or chemotherapeutic(s) to be tested to a growing culture of the microorganisms. After incubation, the size of the inhibition zone demarcating a circular area of no growth from the general lawn of microbial growth is read. The susceptibility of microorganisms for various antibacterial substances can be established in this way. This can be used as a guidance for the selection of an appropriate antimicrobial therapy for the treatment of infections caused by the microorganism in question. Susceptibility testing of microorganisms can be carried out by applying either a suspension of colonies from pure isolates or biological fluids containing the infected microorganism directly on a growth medium.

Devices for the determination of the susceptibility of microorganisms are described in U.S. Pat. No. 3,416,998, DK-C-137089 and SE-C-403382. U.S. Pat. No. 3,416,998 relates to a dried, transparent sheet of agar, in which an active substance, such as a chemotherapeutic agent or the like has been incorporated. These agar reagent sheets can i.a. be produced by the dropping of agar incorporated with the reagent on a moving sheet of plastic material. After the agar reagent sheet has dried the plastic material is removed, whereafter pieces of suitable shapes and sizes are cut and are ready to be used. These are intended to replace i.a. antibiotic discs. DK-C-137089 concerns an indicator for the determination of the susceptibility of microorganisms comprising an absorbing carrier, on which growth medium mixed with bactericides has been applied, and on one side of which a moisture-proof layer has been applied. In SE-C-403382 is disclosed means in which the active substance is applied on the growth medium with the aid of a porous carrier. The concentration of the active substance is said to vary continuously along the whole length of the carrier. From this patent is evident that the active substance is essentially transferred from the porous carrier to the cultivation medium in the longitudinal direction of the carrier, the consequence of which is that in the cultivation medium it is not possible to achieve a variation of the concentration of active substance with such an accuracy that it can be read against a pre-determined scale. According to this patent it is also possible to apply two active substances on the growth medium, but only in such a way that concentrations of the substances varying in two directions perpendicular to each other are achieved.

Susceptibility testing of microorganisms using biological fluids can further be exemplified in more detail by describing a method for the determination of the suceptibility of urinary pathogens to antibacterial substances. In this method a so called dip-slide is used, i.e. a rectangular carrier coated with a growth medium for microorganisms, e.g. a suitable agar medium. This dip-slide is e.g. attached to a lid, which fits to a tube. The dip-slide is dipped into a urine specimen, whereby the specimen with the bacteria in it is exposed to the agar surface. Thereafter one or more so called antibiotic discs are applied on the agar surface. These are small discs of a porous material, which have been impregnated with a predetermined amount of an antibacterial agent. When these discs are in contact with the agar surface the antimicrobial agent diffuses out into the agar medium. After applying the discs to the dip-slide, it is placed into a tube, which is then sealed. Thereafter the dip-slide is incubated over night in an incubator (a temperature of about 37° C.) after which the dip-slide is removed from the tube. The results are read by looking for the appearance of an inhibition zone, i.e. a zone with no or very little bacterial growth, and measuring the diameter of this zone. This gives an indication on whether the antibiotic being tested may be effective for the treatment of an infection caused by the microorganism in question. This method is described inter alia in Chemotherapy 25:227–232 (1979) and The Practioner, vol. 224, 931–934, September 1980. The disadvantages with this method are among others the difficulty of handling such a technique in out-patient care centres, as the antibiotic discs due to their small size must be applied by using tweezers or a needle. Further there is a certain risk of infection when reading results of the susceptibility testing since it is necessary to remove the dip-slide from the outer tube. The size of the inhibition zone has to be measured manually and compared to a set of different interpretive templates for different antibiotics, which is a time consuming procedure. At the same time there are technical disadvantages associated with the porous antibiotic discs as diffusion of antibiotics therefrom to the agar layer does not always take place uniformly due to variations in the porosity of the paper of the agar layer and differences in the physico-chemical properties of different antibacterial agents. This is valid for all porous carriers and thus for all the above-mentioned means.

SUMMARY OF THE INVENTION

The present invention relates to a device for susceptibility testing of microorganisms comprising a transparent, sealable container, a rectangular carrier coated with a medium suitable for the growth of microorganisms, means for sealing the container, to which means the carrier may be optionally attached, and a rectangular, transparent, non-porous, inert test strip which is to be applied to the surface of the medium on which the microorganisms grow, with one side of the test strip having two or more antimicrobial substances applied in such a manner that one substance is present in a concentration gradient having a maximum at one end of the test strip and the other substance in a concentration gradient having a maximum at the opposite end, and that there is a zone between the gradients in which there is no substance, and that the concentration gradients of the two substances exhibit their minima at the respective part on the test strip next to the above-mentioned substance-free zone, and on the other side of the test strip there is a scale for direct reading of the susceptibility in which the predefined concentration gradient has been adapted to the reading scale. The test strip is optionally provided with a grip.

DETAILED DESCRIPTION

Figure 1:
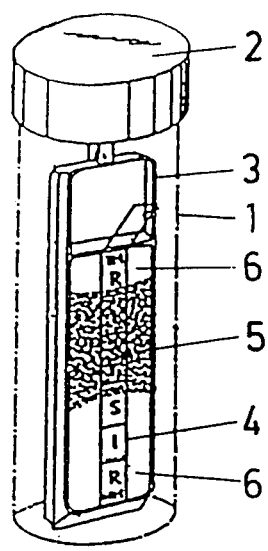
FIG. 1 shows one embodiment of the device according to the invention.

FIG. 1 shows one embodiment of the device according to the invention comprising a transparent tube 1, a rectangular carrier 3 in the form of a dip-slide on which there is an agar layer, and a lid 2, which is connected to the dip-slide. The dip-slide shown in the figure has been dipped for example in a urine specimen, whereafter a test strip 4 having an antimicrobial substance has been applied to the agar surface and the device has been sealed. The test strip is for example of the type illustrated in more detail in FIGS. 2 and 3. The whole device is thereafter incubated over night at about 37° C. Growth of bacteria is shown at 5, while an inhibition of bacterial growth is shown at 6, where the antibiotic concentration present is enough to inhibit bacterial growth. As is evident it is simple to read the result directly, without having to remove the dip-slide from the tube 1.

Figure 2:
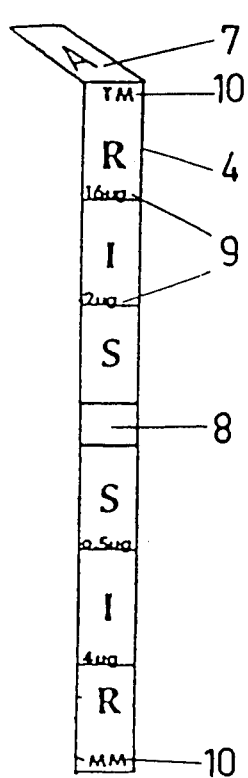
FIGS. 2 and 3 show in more detail one embodiment of a test strip, which is a part of the device.
Figure 3:
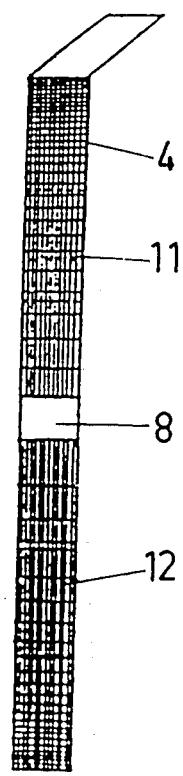

In the embodiment of test strip 4 shown in FIGS. 2 and 3 the test strip is provided with a grip tab 7 which is an angular bending of one end of the test strip. Two antimicrobial substances are applied on one side of the test strip in such a way that one of the substances exhibits a concentraton gradient having a maximum at the end of the test strip integral with the grip tab, while the other substance exhibits a concentration gradient having a maximum at the other end of the test strip. Between these two gradients is a zone 8 where there is no substance present. The other side of the test strip is graded with a scale. FIG. 2 shows the side of the test strip having a scale. The letters R, I and S indicates resistant, intermediate and sensitive categories of susceptibilities to the antibiotic in question. Equally exact concentrations of the substances can be shown (9 in FIG. 2). The code for the antibiotic used can be applied on the space indicated with 10. In FIG. 3, the side of the test strip on which the antimicrobial substances are applied is shown. Two antimicrobial substances are indicated by 11 and 12, and the concentration maxima located in the respective end of the carrier and the minima at respective borders to the zone 8.

In the embodiment shown the container is round, but it can also have an another shape, e.g. oval or square.

Materials suitable for the test strip and container according to the present invention are transparent, inert polymeric materials of a natural or synthetic origin, for example acrylic plastics, styrene plastics, vinyl chloride plastic or glass. They do not have to be of the same material.

Different types of interpretive scales can be used in accordance with the invention, for example a numerical scale.

Growth media containing a gelling agent such as agar-agar and the like can be applied on the rectangular carrier. Nutritive supplements necessary for the growth of the microorganisms can in a manner known per se be added to this medium.

The term "microorganisms" comprise bacteria, such as enterobacteriaceae, staphylococci, streptococci, hemophilus, neisseriaceae, bacteroides, and clostridia, virus and fungi, such as moulds, yeasts, e.g. candida.

The term "antimicrobial substance" refers to one or a combination of more than one antimicrobial substances. Antimicrobial substances comprise antibiotics, for example aminoglycosides, $\beta$-lactam antibiotics, macrolide antibiotics, polymyxins, polypeptides and other chemotherapeutics such as sulfonamides, antimycotics, such as polyene antibiotics, for example amphotericin, griseofulvin, 5-fluorocytosine and imidazoles, antiviral agents, such as amantadine and interferon.

The concentration gradient of the antimicrobial substance on the test strip can be applied in a manner known per se, for example by precision micropipetting.

With the device according to the present invention it is easier to carry out susceptibility testing in out-patient care centres. It is much easier to apply a strip with the help of a grip tab, on the agar surface of a dip-slide than to apply antibiotic discs using tweezers or the like. Further, the risk of infection for the staff working with the test is eliminated, as the reading of the result can be carried out directly without having to remove the dip-slide from the tube as the interpretive scale marked on the test strip gives an immediate answer. This gives accurate and reproducible results and is time-saving, as it does not require, like in other methods, the use of templates which are based on approximations derived from comparisons of inhibition zone sizes and MIC (Minimum Inhibitory Concentration) values. Further, an instantaneous diffusion of antimicrobial substance from the strip to the agar is achieved with a non-porous test strip, which in accordance with the invention results in a stable and continuous concentration gradient in the reaction layer, thus eliminating the interferene that may arise when using porous carriers. An exact amount of the substance in a well defined gradient along the strip, is transferred to the test surface, thereby giving with good reproducibility an exact and accurate measure of the susceptibility of the microorganism for the antimicrobial substance being tested.

We claim:

1. A device for susceptibility testing of microorganisms, comprising:

a sealable container including a body having a transparent sidewall through which a space defined within the container body may be observed from externally of the container, and a sealing means for sealing an openable mouth of the container body for providing thereby a sealed container;

a rectangular carrier having two opposite ends and two opposite faces, at least one of said faces bearing a coating of a medium suitable for growing microorganisms; said carrier being sized to be inserted in said space, so that, in use, the carrier may be inserted in said space and said at least one face thereby disposed for observation from externally of said scaled container through said transparent sidewall;

a rectangular test strip having two opposite ends and two opposite faces, said test strip being sized so that, in use, one of said faces thereof may be aligned with and attached facewise against said coating of medium on said one face of said carrier and the carrier having said test strip thereby applied facewise thereon disposed in said space and said sealing means operated to seal said mouth of said container body;

said test strip being made of non-porous material and having applied thereon on said one face thereof two different antimicrobial substances, in two longitudinally spaced, longitudinally extending zones, each having one end located generally centrally of the test strip and an opposite end located generally adjacent a respective end of said test strip;

each said antimicrobial substance exhibiting a concentration gradient having a maximum located generally adjacent a respective said end of said test strip and a minimum located generally centrally of said test strip, and there being disposed between said two zones of applied antimicrobial substances a zone in which neither of said two antimicrobial substances is present; and said test strip bearing a scale extending longitudinally thereon along both of said two zones and exhibiting marks which are susceptible of being directly read as indications of the concentration gradient of the respective antimicrobial substance at each of a plurality of locations therealong while said test strip remains applied against said one face of said carrier and contained in said space in said sealed container.

2. The susceptibility testing device of claim 1, wherein:
said test strip is made of transparent material so that said scale may be read through said material thereof.

3. The susceptibility testing device of claim 2, wherein:
said test strip is mainly planar and further comprises a handle projecting and includes a grip tab projecting out of a main plane thereof to facilitate applying the test strip to said coating of medium on said one face of said carrier.

4. The susceptibility testing device of claim 3, wherein:
said grip tab is provided so as to be integral with said test strip.

5. The susceptibility testing device of claim 2, wherein:
said carrier is attached to said sealing means so as to depend therefrom into said space when said sealing means seals said openable mouth of said container body.

6. The susceptibility testing device of claim 1, wherein:
each said antimicrobial substance is an antibiotic agent.

7. The susceptibility testing device of claim 1, wherein:
each said antimicrobial substance is a chemotherapeutic agent.

8. The susceptibility testing device of claim 1, wherein:
each said antimicrobial substance is an antimycotic agent.

9. The susceptibility testing device of claim 1, wherein:
each said antimicrobial substance is an antiviral agent.

10. The susceptibility testing device of claim 1, wherein:
said test strip is made of an inert polymeric material.

11. The susceptibility testing device of claim 10, wherein:
said inert polymeric material is selected from the group consisting of acrylic plastic material, styrene plastic material and vinyl chloride plastic material.

12. The susceptibility testing device of claim 1, wherein:
said test strip is made of an inert glass.

13. A device for susceptibility testing of microorganisms, comprising:
a sealable container including a body having a transparent sidewall through which a space defined within the container body may be observed from externally of the container, and a sealing means for sealing an openable mouth of the container body for providing thereby a sealed container;

a rectangular carrier having two opposite ends and two opposite faces, at least one of said faces bearing a coating of a medium suitable for growing microorganisms; said carrier being sized to be inserted in said space, so that, in use, the carrier may be inserted in said space and said at least one face thereby disposed for observation from externally of said scaled container through said transparent sidewall;

a rectangular test strip having two opposite ends and two opposite faces, said test strip being sized so that, in use, one of said faces thereof may be aligned with and attached facewise against said coating of medium on said one face of said carrier and the carrier having said test strip thereby applied facewise thereon disposed in said space and said sealing means operated to seal said mouth of said container body;

said test strip being made of non-porous material and having applied thereon on said one face thereof two different antimicrobial substances, in two spaced-apart zones;

each said antimicrobial substance exhibiting a concentration gradient having a maximum located at one end of a respective said zone and a minimum located at the opposite end of the respective said zone, and there being disposed between said two zones of applied antimicrobial substances a zone in which neither of said two antimicrobial substances is present; and said test strip bearing scale means extending longitudinally thereon along each of said two zones and exhibiting marks which are susceptible of being directly read as indications of the concentration gradient of the respective antimicrobial substance at each of a plurality of locations therealong while said test strip remains applied against said one face of said carrier and contained in said space in said sealed container.

* * * * *